(12) United States Patent
Kollgaard

(10) Patent No.: US 7,448,270 B2
(45) Date of Patent: Nov. 11, 2008

(54) SINGLE-SIDE ULTRASONIC INSPECTION SYSTEMS AND METHODS

(75) Inventor: Jeffrey R. Kollgaard, Kent, WA (US)

(73) Assignee: The Boeing Company, Chicago, IL (US)

( * ) Notice: Subject to any disclaimer, the term of this patent is extended or adjusted under 35 U.S.C. 154(b) by 401 days.

(21) Appl. No.: 11/263,746

(22) Filed: Nov. 1, 2005

(65) Prior Publication Data

US 2007/0095140 A1    May 3, 2007

(51) Int. Cl.
G01N 29/26    (2006.01)

(52) U.S. Cl. .............................. 73/633; 73/624; 73/628

(58) Field of Classification Search .................... 73/633, 73/620, 627, 628, 624, 625, 622, 644
See application file for complete search history.

(56) References Cited

U.S. PATENT DOCUMENTS

| 3,204,458 | A | * | 9/1965 | Gillen ...................... 73/861.26 |
| 4,252,024 | A | * | 2/1981 | Hurwitz ....................... 73/603 |
| 4,674,334 | A | * | 6/1987 | Chimenti et al. .............. 73/627 |
| 5,154,081 | A | | 10/1992 | Thompson et al. |
| 5,585,564 | A | * | 12/1996 | Brunty et al. .................. 73/634 |
| 5,698,787 | A | | 12/1997 | Parzuchowski et al. |
| 6,234,024 | B1 | * | 5/2001 | Brunty et al. .................. 73/634 |
| 6,431,002 | B1 | * | 8/2002 | Aijima .......................... 73/620 |
| 6,722,202 | B1 | | 4/2004 | Kennedy et al. |
| 6,848,312 | B2 | | 2/2005 | Georgeson |
| 6,920,790 | B2 | | 7/2005 | Huang et al. |
| 6,981,418 | B1 | * | 1/2006 | Mueller ........................ 73/633 |
| 7,234,353 | B2 | * | 6/2007 | Mueller ........................ 73/618 |
| 2005/0145033 | A1 | | 7/2005 | Bossi et al. |

OTHER PUBLICATIONS

Christopher Smith, Igor Komsky, *DC-9 Tee Cap Inspection, FAA Centers of Excellence 3rd Joint Annual Meeting*, 2003.
Masoud Rais-Rohani, Gary Quinn, Christopher Eamon, Amy L. Keesecker, *Finite Element Analysis and Sizing Optimization of an Advanced Design Concept for a Composite Sail Structure, 45th AIAA/ASME/ASCE/AHS/ASC Structures, Structural Dynamics & Materials Conference*, Apr. 19-22, 2004. American Institute of Aeronautics and Astronautics, Inc., Palm Springs, California.

(Continued)

*Primary Examiner*—Hezron E. Williams
*Assistant Examiner*—Jacques M. Saint-Surin
(74) *Attorney, Agent, or Firm*—Alston & Bird LLP

(57) ABSTRACT

Ultrasonic systems and methods for inspecting a channel member through a skin or panel are provided. The channel member may be a stiffener for an aircraft component such as a trapezoidal stringer attached to a skin of an aircraft fuselage. Transducers of the system are disposed on a side of the skin opposite the channel member. Ultrasonic waves generated on a first side of a skin propagate through the skin, across a channel member attached to a second side of the skin, and through the skin again to be received on the first side of the skin. Times of flight are measured for the collection of time-gated data. A two dimensional C-scan is generated for identifying flaws and irregularities in a structure by way of single-side ultrasonic non-destructive inspection (NDI).

19 Claims, 3 Drawing Sheets

OTHER PUBLICATIONS

T. Demol, P. Blanquet, C. Delebarre, *Optimization Of Linear Array Transducers For Lamb Waves Generation*, Available at http://www.ndt.net/abstract/wendt96/data/557.html, dated Mar. 24, 2005.

Vlad Moshkovich, Alex Passi, Garri Passi, Roustam Safin, *Recent Advances in the Ultrasonic Inspection Recording and Reporting—Instrumentation: Part 2. Straight Beam Inspection and Imaging*, Available at http://www.ndt.net/article/v08n11/passi2/passi2.html, dated Aug. 22, 2005.

Manny Butera, *Online Exclusive: Improving Quality with Ultrasonic C-Span Imaging*, Available at http://www.ceramicindustry.com/CDA/ArticleInformation/features/BNP_Features_Item . . . , dated Aug. 232, 2005.

B. Vagnhammar, L. Ericsson, T. Stepinski, *Ultrasonic Inspection Of Bonded Structures*, Available at http://www.signal.uu.se/Research/NDE/BondTest/BondStr.html, dated Sep. 2, 2005.

U.S. Appl. No. 11/041,499, Not yet published, Kennedy et al.

Ningqun Guo, Peter Cawley, *Lamb Wave Reflection for the Quick Nondestructive Evaluation of Large Composite Laminates*, Materials Evaluation, Mar. 1994, pp. 404-411.

J.L. Rose, A. Pilarski, J.J. Ditri, *An Approach to Guided Wave Mode Selection for Inspection of Laminated Plate*, Journal of Reinforced Plastics and Composites, vol. 12—May 1993, pp. 536-545.

V. Agostini, D. Zoccolan, *Flaw Detection in Composite Plates by Means of Lamb Waves*, http://www.ndt.net/article/wcndt00/papers/idn275/idn275.htm , Nov. 14, 2005, pp. 1-6.

K.S. Tan, N. Guo, B.S. Wong, C.G. Tui, *Comparison of Lamb Waves and Pulse Echo in Detection of Near-Surface Defects in Laminate Plates*, NDI&E International, vol. 28, No. 4, 1995, pp. 215-223.

Brian James Tucker, *Ultrasonic Plate Waves In Wood-Based Composite Panels*, Dissertation, Washington State University Department of Civil and Environmental Engineering, Aug. 2001, pp. i-xiii and 1-113.

Review of Progress in Quantitative NDE, Western Washington University, Bellingham, Washington, Jul. 14-19, 2002, 1-222.

\* cited by examiner

SINGLE-SIDE ULTRASONIC INSPECTION SYSTEMS AND METHODS

FIELD OF THE INVENTION

Embodiments of the present invention relate generally to non-destructive inspection devices and methods. More particularly, embodiments of the invention relate to devices and methods for the single-sided ultrasonic inspection of a stiffener attached to a panel.

BACKGROUND OF THE INVENTION

Durability, strength, and reliability are goals that often oppose efficiency in the manufacturing of many sorts of structures. In order to be both commercially viable and safe, vehicle components in particular should be both light weight and structurally sound. In meeting both challenges, modern vehicle components such as aircraft fuselages and wings are often designed to include thin external skins and stiffening members attached to the skins within the interiors of the components. The integrity of such a component relies on the condition of the skin, the condition of the stiffening member, and on the condition of the bond joining the two. Ultrasonic non-destructive inspection (NDI) technologies are emerging so that in situ inspections of a vehicle and its components can be accomplished with little or no disassembly.

Ultrasonic NDI technologies are available for inspecting an external skin of a component of a vehicle by disposing a transducer and a sensor along the skin. For example, an apparatus for evaluating the stiffness of a composite plate is described in the U.S. Pat. No. 6,920,790, issued to Huang et al. on Jul. 26, 2003, the contents of which patent is incorporated herein by reference. In the identified patent, a transducer imparts energy into a plate causing a wave to propagate along the plate and the wave is detected by a sensor disposed along the plate. The velocity of the wave is determined and a material stiffness parameter for the plate is calculated based on the velocity. Such calculations are useful in inspecting the condition of a planar or smoothly contoured material such as the external skin of an aircraft fuselage.

Ultrasonic NDI technologies are available for inspecting a stiffening member by disposing a transmitter and a sensor on opposing sides of a stiffening member that is to be inspected. Such technologies are described, for example, in the co-pending U.S. patent application Ser. No. 10/752,890 of Bossi et al., the contents of which patent application, and the contents of the publication thereof, namely United States patent application publication number US2005/0145033 A1, published Jul. 7, 2005, are incorporated herein by reference. In the identified patent application publication, ultrasonic transmitters and sensors disposed within the interior of a structure are magnetically coupled to an apparatus disposed on the exterior of the structure. The transmitters and sensors move within the structure in concert with movements of the external apparatus. This arrangement appears to be useful in a situation where the movement of equipment within the interior of a structure is permitted. A vehicle component such as the fuselage or a wing of an airplane, however, typically has an interior that is partially or wholly obstructed with such things as electrical wires, ventilation ducts, actuating cables, hydraulic control lines, fuel lines, and insulation materials. Thus, inspecting stiffening members in the obstructed interior of a vehicular structure by moving equipment about in the interior is not always convenient, particularly where flight schedules may be affected.

A need exists for convenient and reliable NDI devices and methods that are capable of detecting flaws defined in a stiffening member attached to a skin. Devices and methods are needed for inspecting stiffening members through a skin so that single-sided inspection can be accomplished without disposing inspection equipment within the interior of a structure.

BRIEF SUMMARY OF THE INVENTION

Embodiments of the invention address the above needs and achieve other advantages by providing an ultrasonic inspection system that is capable of single-sided inspection. In particular, the ultrasonic inspection system is capable of inspecting a channel member through a skin, where the channel member and inspection system are disposed on opposite sides of the skin. The inspection system incorporates a first ultrasonic transducer that sends ultrasonic waves into the channel member through the skin, and a second ultrasonic transducer that receives ultrasonic waves from the channel member through the skin. The transducers communicate with a controller and display system for presenting data, optionally as C-scan images, for the detection of irregularities in the channel member or in the bond between the channel member and skin. By sending ultrasonic waves through the skin and across the channel member without accessing the interior of the inspected structure, non-destructive inspection is accomplished by embodiments of the invention with conveniences unavailable in conventional approaches which typically entail at least partial disassembly of a structure under inspection.

In one embodiment, an ultrasonic inspection system is provided for inspecting an elongate channel member attached to a panel such that an elongate channel is defined between the channel member and panel. The system includes a first transducer disposed near the panel opposite a first interface of the channel member, and a second transducer disposed near the panel opposite a second interface of the channel member. The first transducer transmits an ultrasonic signal such that a portion of the signal propagates through the panel and across the channel member to the second transducer.

The ultrasonic inspection system may include a connector that connects the first and second transducers and maintains them spaced at a distance approximately equivalent to the distance between the first and second interface portions of the channel member. The channel member is typically a stiffener for an aircraft component and the panel is typically the skin of the component. The system may further include a display system for presenting a C-scan image of the inspected component, wherein irregularities in the channel member, or in its attachment to the panel, appear as irregularities in the C-scan image.

Embodiments of the present invention also provide a method of inspecting a structure that includes a skin and channel member attached to the skin such that a channel is defined. The method includes transmitting an ultrasonic signal into the structure through the skin such that a portion of the signal propagates across the channel member, partially about the channel, and is received through the skin. Defects in the channel member are detected based upon the received signal.

In various aspects, the method may include moving a transmitting transducer in concert with a receiving transducer in two dimensions near the skin. The method may include measuring the time elapsed between the transmission and receipt of an ultrasonic signal for determining the time of flight of the signal in propagating across the channel member. A C-scan image may be generated based on the amplitude of the received signal.

In another method according to an embodiment of the present invention, a stiffener attached to a panel is inspected utilizing an inspection apparatus that includes a first transducer for transmitting ultrasonic signal and a second transducer for receiving ultrasonic signals. The apparatus is first disposed at a first location near the panel such that portions of the signals transmitted by the first transducer propagate across the stiffener and are received by the second transducer. The apparatus is then disposed at a second location and signals again propagate across the stiffener and are received. The amplitudes of the received signals are measured at the first location and second location. Irregularities are detected in the stiffener by comparing the amplitudes of the signals received at the two locations.

In various aspects, the method may include that an axis defined as passing through both transducers is maintained essentially perpendicular to the stiffener. The method may further include maintaining a distance between the transducers that is essentially the same as the width of the stiffener. The transducers are optionally moved in concert in two dimensions for generating a C-scan display.

BRIEF DESCRIPTION OF THE SEVERAL VIEWS OF THE DRAWINGS

Figure 1:
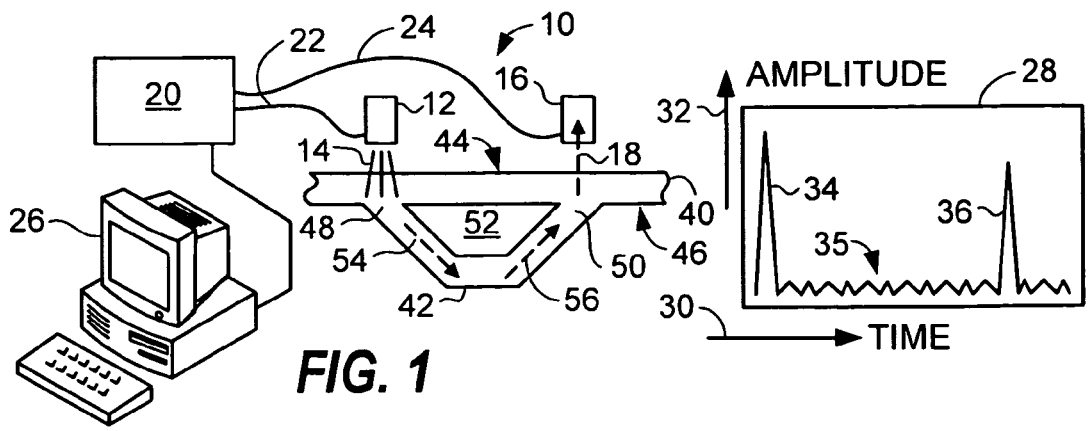
Figure 2:
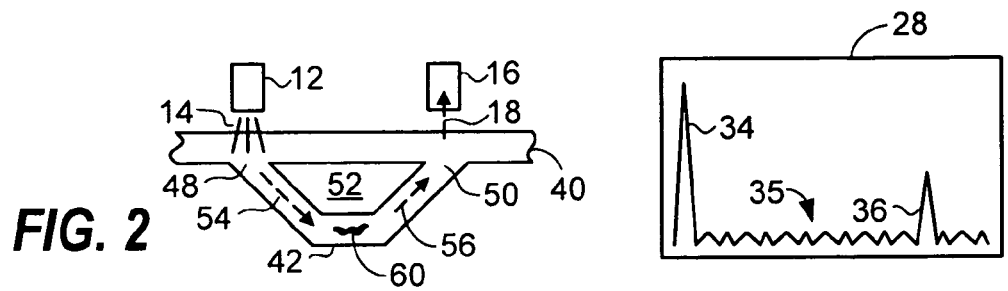
Figure 3:
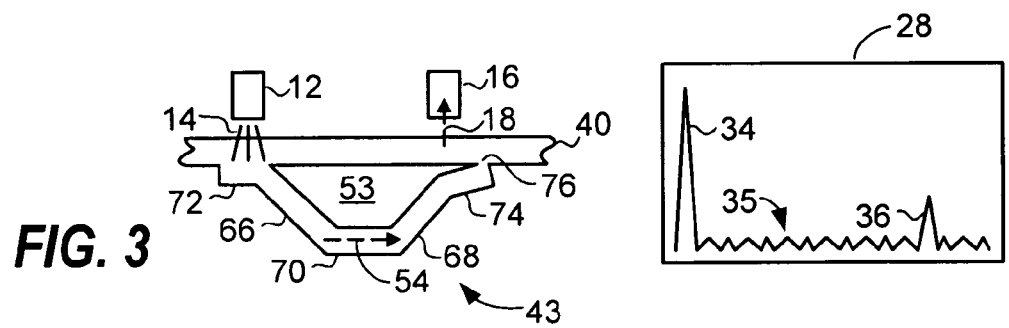
Figure 4:
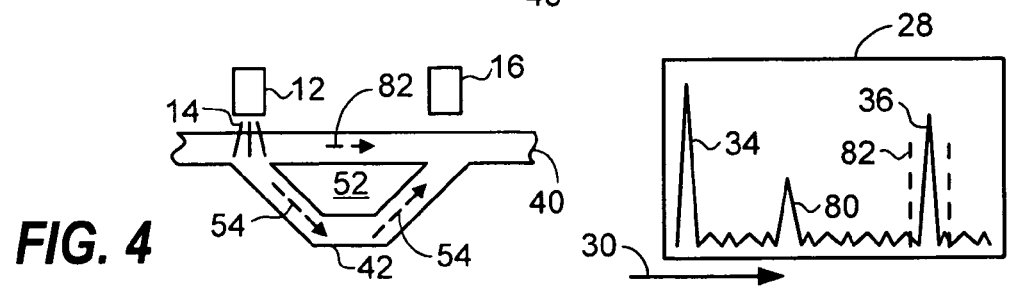
Figure 5:
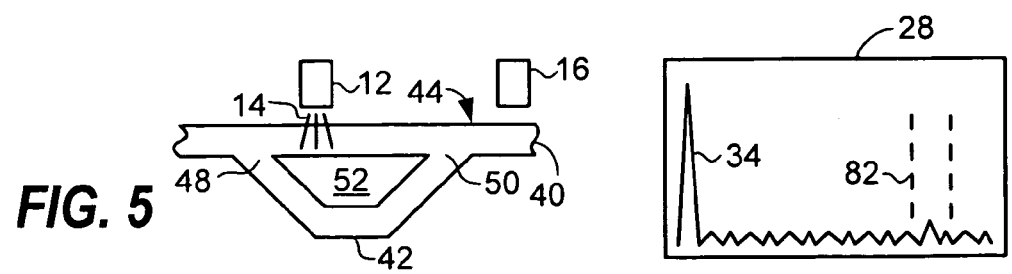
Figure 6:
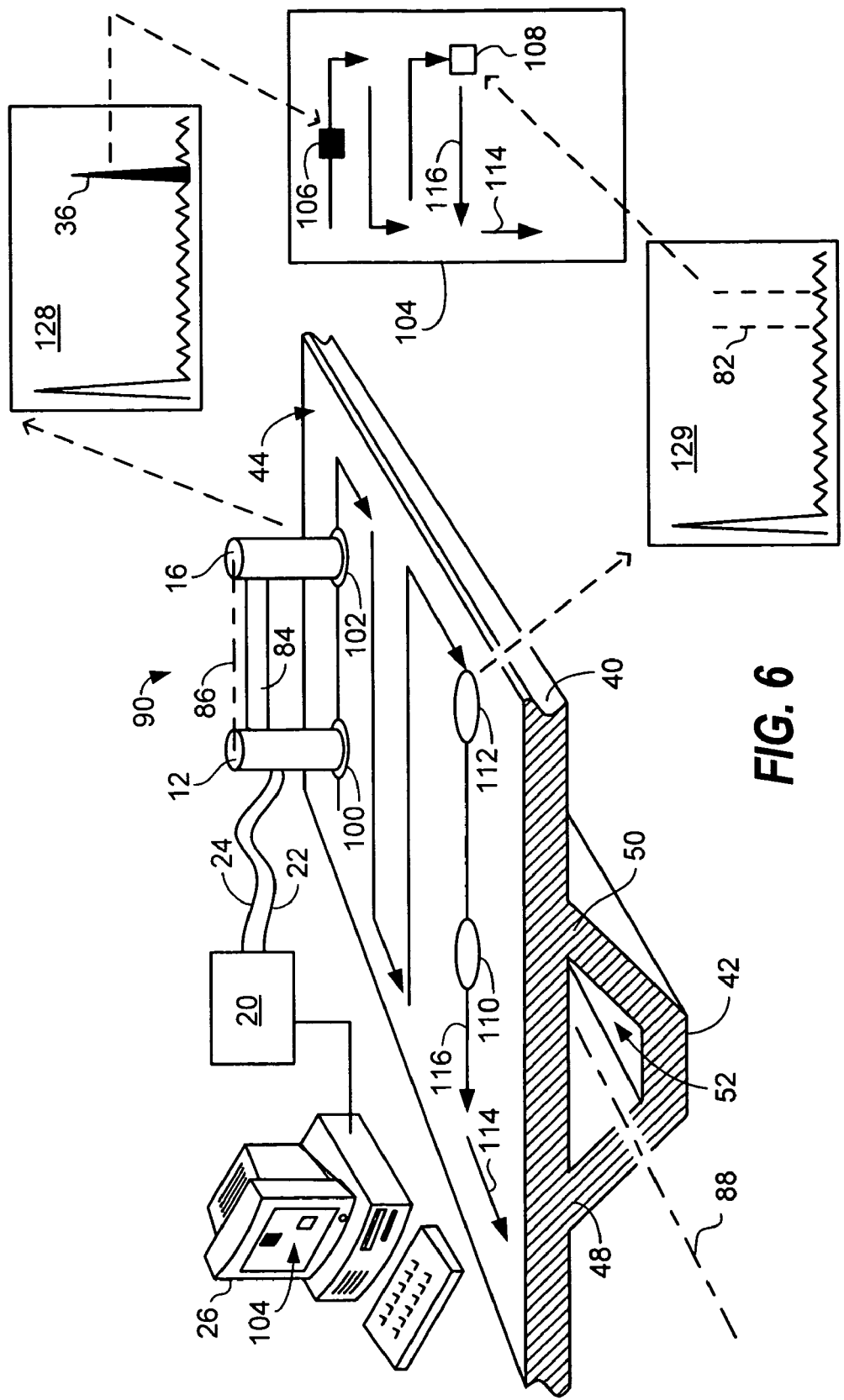
Figure 7:
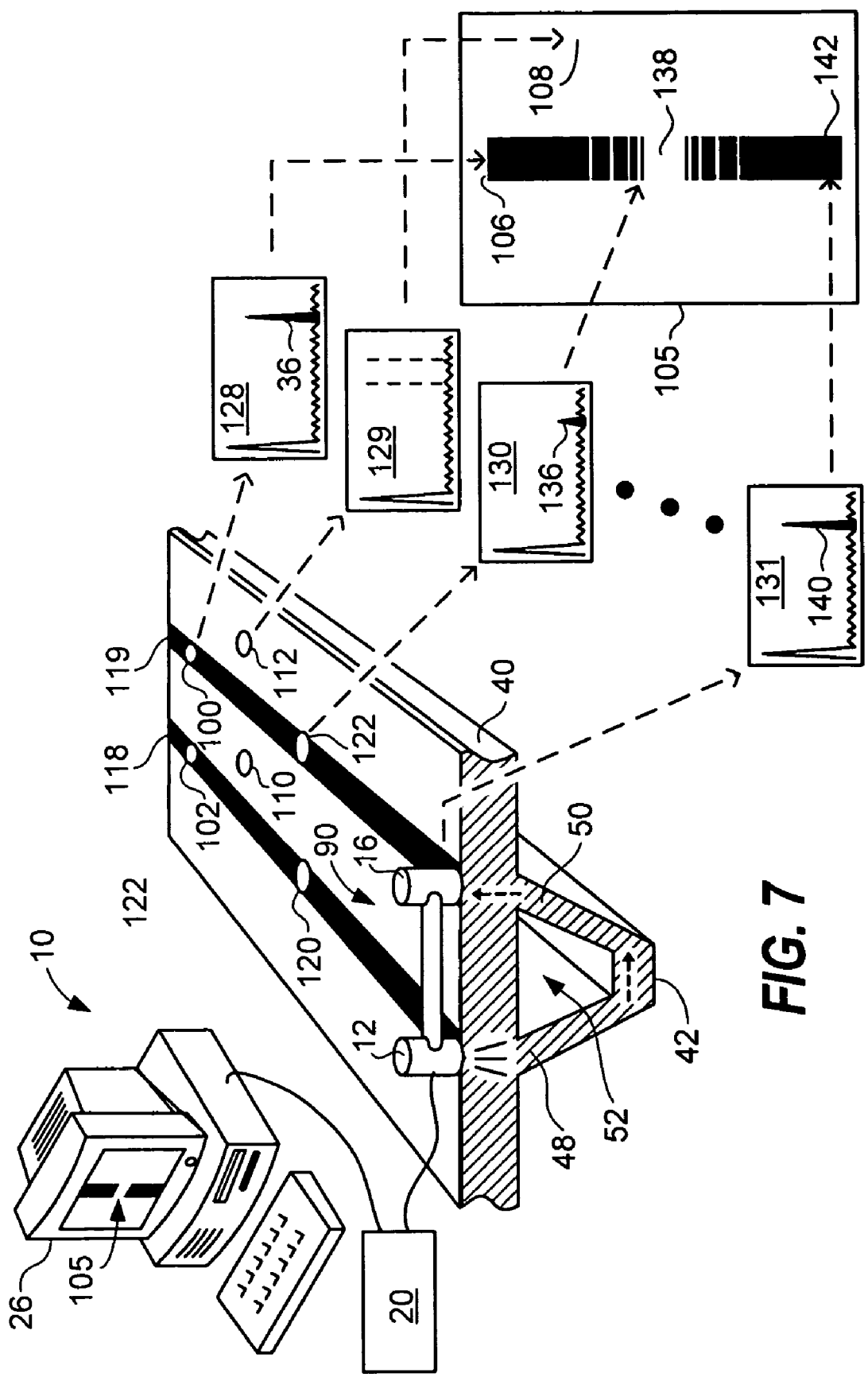

Having thus described the invention in general terms, reference will now be made to the accompanying drawings, which are not necessarily drawn to scale, and wherein:

FIG. 1 is a diagrammatic environmental view of an ultrasonic inspection system, according to an embodiment of the invention, disposed over a channel member and presenting a plot demonstrating the good condition of the channel member;

FIG. 2 is a diagrammatic environmental view of the inspection system of FIG. 1 disposed over a damaged portion of the channel member;

FIG. 3 is a diagrammatic environmental view of the inspection system of FIG. 1 inspecting a damaged trapezoidal hat stringer of an aircraft component;

FIG. 4 is a diagrammatic environmental view of the inspection system of FIG. 1 configured to suppress direct path signal interference by evaluating data pulses in a time gate;

FIG. 5 is a diagrammatic environmental view of the inspection system of FIG. 1 displaced relative to the channel member such that a data pulse is not received in the time gate of FIG. 4;

FIG. 6 is a diagrammatic perspective environmental view of the inspection system of FIG. 1 moved about over an inspected structure to partially populate a C-scan with data related to the condition of the structure; and FIG. 7 is a diagrammatic perspective environmental view of the inspection system of FIG. 1 having completely populated the C-scan of FIG. 6;

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Referring now to the drawings, an ultrasonic inspection system 10 is shown that includes a first ultrasonic transducer 12 that generally transmits ultrasonic signals 14, a second ultrasonic transducer 16 that generally detects ultrasonic signals 18, a controller 20 that is electronically coupled to the first and second transducers by one or more wireless devices or by respective cabled connections 22 and 24, and a display system 26 electronically coupled to the controller 20. The display system 26 may be a stationary system such as a computer system, or a portable system such as a portable laptop computer system, or other visual presentation system. The controller and display system may be respective parts of a unified system within a common housing that is stationary or portable. The controller 20 energizes and prompts the first transducer 12, by way of the connection 22, to transmit ultrasonic signals 14. In response to detecting ultrasonic signals 18, the second transducer 16 generates an output signal that is received by the controller 20 by way of the connection 22. The controller 20 collects data by way of the second transducer 16 and presents representations of the data through the display system 26. The representations presented provide information about the structure under inspection by the system 10. A two-dimensional mapping referred to herein as a C-scan is preferably presented by the display system 26 as shown in FIG. 7. The C-scan described in the following with reference to FIG. 7 may be understood by first considering the inspection scenarios described in FIGS. 1-6 which establish how the C-scan in FIG. 7 relates to the condition of a structure under inspection.

In conjunction with or in lieu of a two-dimensional mapping such as a C-scan (FIG. 7), the display system 26 may present a plot 28 representing time on a horizontal axis 30 and pulse amplitudes on a vertical axis 32. Such plots, which are shown in FIGS. 1-7, may be referred to as a plot of amplitude versus time. In the exemplary plot 28 illustrated in FIG. 1, a triggering pulse 34 coincides with and represents the transmission of an ultrasonic signal 14 into a structure by the first transducer 14. The triggering pulse 34 is sometimes referred to as the "main bang" in ultrasonic inspection system terminologies. It represents the sending of ultrasonic energy into a structure and provides a trigger for time sweeps on pulse analyzing electronics devices such as oscilloscopes. Time measurements are generally conducted with the triggering pulse 34 serving as an origin for the time axis 30. Minor peaks and valleys following the triggering pulse 34 represent noise or background signals 35 in the controller 20 or the second transducer 16.

The data pulse 36 represents the detection and measurement of an ultrasonic signal 18 received by the second transducer 16. The disposition of the data pulse 36 along the time axis 30 represents the travel time, or time of flight (TOF), of ultrasonic waves from the first transducer 12 to the second transducer 16. Where ultrasonic waves travel through a structure along a particular path, the data pulse 36 occurs along the time axis 30 according to the length of the path and according to the speeds at which the waves travel through the materials in the path. The amplitude of the data pulse 36 represents the amplitude of the ultrasonic signal 18 as measured by the second transducer 16.

While the plot 28 may represent the result of a snapshot inspection including a single sweep across the time axis 30 after a single ultrasonic pulse by the first transducer 12, the system 10 preferably cycles so that the plot 28 presents time-varying data as the transducers are moved. The controller 20 may cycle the sending and receiving of pulses at a pulse repetition rate, for example between one and ten kilohertz, and update data presentations with each cycle.

A raw data stream including data regarding trigger pulses, data pulses, and all events of the inspection system 10, which may be time-stamped events, may be recorded in whole or in part for on-going analysis or later analysis. For example, the controller 20 or the display system 26 may comprise a storage medium for recording data. As will be further discussed in the following, the ultrasonic inspection system 10 may comprise a movement encoder for correlating collected inspection data with real locations along an inspected structure. Data collected by the second transducer 16 and such an encoder may be correlated in real time for physically locating flaws and irregularities in an inspected structure or may be recorded for later processing that may include visualizations such as plots and C-scans presented by the display system 26.

As described in the following with reference to FIGS. 1-5, which represent several respective NDI scenarios, the amplitude of the data pulse 36 represents an inspection parameter by which the ultrasonic inspection system 10 is sensitive to the presence of flaws and irregularities in a structure. With particular regard to the inspection scenario of FIG. 1, ultrasonic inspection system 10 is deployed to inspect a structure that comprises a skin 40 and a channel member 42. The ultrasonic inspection system 10 is generally disposed on a side of the skin 40 that is opposite the channel member 42 in that the first and second transducers 12 and 16 are disposed near a first surface 44 of the skin whereas the channel member is attached to the second surface 46 opposing the first surface. In particular, the channel member 42 comprises a first interface portion 48 and a second interface portion 50 each present on the second surface 46 of the skin 40 such that a channel 52 is defined. The channel 52 is surrounded by the second surface 46 and the channel member 42.

The structures shown under inspection in FIGS. 1-5 are illustrated in partial cross-sectional views taken perpendicular to generally elongate structures as shown in the perspective views of FIGS. 6-7. Thus, for example in FIG. 1, the skin 40 represents a somewhat planar member like a panel, the channel 52 represents an elongate channel, and the interface portions 48 and 50 represent elongate edge portions of an elongate channel member 42 that are interfaced with, attached or bonded to, or otherwise present on the second surface 46 of the skin.

Furthermore, the skins and panels illustrated in the accompanying drawings are shown as being either generally planar or as having smoothly varying contours. Nonetheless, the real world skins and panels to which these descriptions relate can have more complex shapes. For example, the skin 40 of FIG. 1 may be a small portion of an aircraft fuselage that actually has a circular full cross section. The portion of the skin 40, shown in partial cross-sectional view in FIG. 1, may be such a small portion of such a fuselage that the slight circular arch in the portion is not detectable in the figure. On the other hand, the skin 40 of FIG. 1 may be an exactly planar panel. Exactly planar panels and contoured skins may be stiffened by attached channel members without contradiction and within the scope of these descriptions.

Although the ultrasonic inspection system 10 can be utilized to inspect a wide variety of structures, the structures illustrated in FIGS. 1-5 relate to aircraft components such as wings and fuselages that comprise skins 40 and channel members 42-43. The channel members are attached to the skins for stiffening the components. Such channel members are often referred to in the aircraft industry as stiffeners, stringers, and hat stringers.

While the first and second transducers 12 and 14 are each generally movable along the first surface 44 of the skin 40, in the instant of FIG. 1 they are disposed to respectively send and receive ultrasonic signals through the skin 40 and across the channel member 42 for inspecting the channel member. In particular, in FIG. 1, the first transducer 12 is disposed opposing the first interface portion 48 for coupling or guiding ultrasonic waves through the skin and into the channel member 42. The first transducer 12 generally impinges ultrasonic waves, represented by the first signal 14, onto the first surface 44. A portion of the ultrasonic energy impinged upon the first surface transmits through the skin and enters the channel member 42 as represented by the signal 54. Ultrasonic waves then travel across or through the channel member 42 and partially about the channel 52 as represented by the signal 56. Finally, ultrasonic waves that have crossed the channel member transmit through the skin as represented by the signal 18. In FIG. 1, the second transducer 16 is disposed opposing the second interface portion 50 for receiving the signal 18.

The first transducer 12 comprises a device for converting an electrical pulse into an ultrasonic pulse, and the second transducer 16 comprises a device for converting a received ultrasonic pulse into an electrical pulse. Devices which serve in both capacities are commercially available and so the first and second transducers may comprise similar or essentially identical devices. For example, the first transducer 12 and second transducer 16 may each comprise a respective piezoelectric instrument operable in an ultrasonic frequency range such as ten kilohertz to two megahertz. Ultrasonic waves may be conveyed between the transducers and the skin by contact or by dry or wet coupling. Typical commercially available transducers transmit ultrasonic longitudinal waves along an axis, and where the first and second transducers of the system 10 comprise such transducers, their axes are generally oriented normal (orthogonal) to the skin 40.

While longitudinal waves propagating through and emanating from the skin 40 may be represented respectively by the signals 14 and 18 of FIGS. 1-4, other types of ultrasonic waves are represented in these figures also. For example, the signal 54 may represent a lamb wave that propagates across the channel member 42. Ultrasonic waves propagating through a planar material from one surface of to an opposing surface are generally nominally referred to herein as longitudinal waves that generally travel along a particular axis. Ultrasonic waves propagating along a planar material are generally nominally referred to herein as lamb waves that can follow a contour.

Impinging longitudinal waves onto the skin at lower ultrasonic frequencies may be preferable for energizing lamb waves that propagate across the channel member. For example, the first transducer 12 may comprise a wet coupled ultrasonic device operative in the five hundred kilohertz to one megahertz frequency range. For further example, the first transducer 12 may comprise a dry coupled ultrasonic device in the fourteen to fifty four kilohertz range.

It should be noted that despite language herein referring to longitudinal waves and lamb waves, the waves represented by signals in the figures may actually contain mixtures of wave types and multiple frequency components. Indeed, in transmitting through the skin 40 and propagating across the channel member 42, ultrasonic energy may convert within the structure from one or more particular types of waves to other types of waves. Furthermore, ultrasonic energy may convert within the structure from particular discrete frequency components to particular other components or may be generally transferred into broad ultrasonic frequency domains. Thus, without limitation to particular types of ultrasonic waves and particular ultrasonic frequency ranges, ultrasonic energy is generally sent into the inspected structure by the first transducer 12, and ultrasonic energy is generally received from the structure by the second transducer 14.

FIG. 1 represents an inspection scenario where the channel member 42 is in good condition and contains no flaws or irregularities. The amplitude of the data pulse 36 in the plot 28 in FIG. 1 represents a benchmark measure of the signal 18 to which data pulses in the plots of FIGS. 2-5 are to be compared for inspecting the channel member 42 in various conditions, some of which are compromised by flaws and irregularities. In FIGS. 2-5, for simplicity the first transducer 12 and second transducer 16 of the system 10 are shown in dispositions relative to inspected structures without repetitively showing the display system 26 and controller 20 to which the transducers are nonetheless coupled.

FIG. 2 represents an inspection scenario where the channel member 42 contains a hidden flaw 60. The channel members 42, and the skins 40, are optionally constructed of layered composite materials comprising carbon fibers impregnated with epoxy resin. The flaw 60 may represent an area of the channel member where layers of composite material have delaminated, or may represent a buckle or rupture in the channel member. It has been found that some types of impact to an aircraft component can cause hidden damage to a channel member without causing visible damage to the skin and without causing the channel member to detach from the skin. Such damage is represented in FIG. 2 by the flaw 60 which is hidden within the channel member away from the skin 40.

The flaw 60 is detectable as provided by the benefits and advantages of embodiments of the inventive ultrasonic inspection system 10 and by way of inventive methods in which the system 10 is deployed. In particular, the first and second transducers 12 and 16 are disposed in FIG. 2 similarly as in FIG. 1. The first transducer impinges ultrasonic waves, as represented by the signal 14, onto the structure that comprises the skin 40 and channel member 42. Ultrasonic waves enter the channel member as represented by the signal 54. Ultrasonic waves propagating across the channel member 42 are attenuated by the flaw 60 in the scenario of FIG. 2. The ultrasonic waves that travel partially about the channel 52 and transit the second interface portion 50 of the channel member 42 are similarly attenuated as represented by the reduced signal 56. The ultrasonic waves that then travel through the skin, as represented by the reduced signal 18, express the attenuation that occurred at the flaw 60. The plot 28 displays a reduced data pulse 36 that may alert a human operator that the ultrasonic inspection system 10 has detected the flaw 60. For example, a threshold may be defined between the amplitude of the data pulse 36 in FIG. 1 and the amplitude of the data pulse 36 in FIG. 2, wherein the reduction of the data pulse to an amplitude below the threshold represents the detection of a flaw in the channel member.

In FIG. 3, the illustrated channel member 43 relates particularly to a trapezoidal hat stringer. As shown in FIG. 3, a trapezoidal hat stringer 43 comprises a pair of generally planar web members 66 and 68 respectively attached to a generally planar cap member 70 along opposing sides of the cap member. Webs 66 and 68 extend from the cap member 70 and terminate in respective flanges 72 and 74 that are generally attached or bonded to the skin 40.

In the inspection scenario illustrated in FIG. 3, the flange 74 which connects the web member 68 to the skin 40 is partially detached from the skin at a compromised bond line 76. The ultrasonic inspection system 10 is capable of detecting this irregularity. The first transducer impinges ultrasonic waves, as represented by the signal 14, onto the skin 40. Ultrasonic waves, as represented by the signal 54, enter the hat stringer 43 by way of the first flange 72 which is well bonded to the skin. These waves propagate across the hat stringer 43, partially about the channel 53 defined between the skin and the hat stringer, and enter the second flange 74. Ultrasonic waves passing from the second flange 74 to the skin 40 are attenuated at the compromised bond line 76 as represented by the reduced signal 18 received through the skin by the second transducer 16. The plot 28 of FIG. 3 displays a reduced data pulse 36 that may alert a human operator that the ultrasonic inspection system 10 has detected the compromised bond line 76.

In the inspection scenarios illustrated in FIGS. 1-3, only the triggering pulse 34 and the data pulse 36 are shown to rise appreciably above the noise or background signals 35 in the plots 28. In the inspection scenario illustrated in FIG. 4, a direct-path pulse 80 precedes the data pulse 36. In this scenario, like in the scenarios of FIGS. 1-3, a portion of the signal 14 from the first transducer 12 propagates across the channel member 42 partially about the channel 52 as represented by the signal 54. However, in this scenario, unlike the scenarios of FIGS. 1-3, a portion of the signal 14 propagates along the skin 40 as represented by the direct-path signal 82 and reaches the second transducer 16 as represented by the direct-path pulse 80 in the plot 28. The path along the skin that the signal 82 travels is different from the path across the channel member that the signal 54 travels and thus the direct path pulse 80 and the data pulse 36 are separated along the time axis of the plot 28. In particular in FIG. 4, the direct path along the skin between the transducers is shorter than the path across the channel member. Thus the direct-path pulse 80 precedes the data pulse 36 relative to the triggering pulse 34. In this scenario, the direct-path pulse 80 represents noise in the plot 28 at least with regard to detecting irregularities in the channel member or its bond to the skin.

FIG. 4 represents a principle by which noise may be discriminated from data pulses 36. A time interval, as represented by the gate 82, situated along the time axis 30 about the expected time of the data pulse 36 can be established relative to the triggering pulse 34. Noise components in the plot 28 can be omitted from consideration by collecting data regarding only signals that fall within the gate 82 relative to the triggering pulse 34.

FIG. 5 represents an inspection scenario in which the first and second transducers 14 and 16 are disposed out of alignment with opposing interface portions of the channel member 42. The first and second transducers 14 and 16 are generally movable, optionally in concert with each other, near the first surface 44 of the skin 40. If the transducers are generally moved about along the skin, alignment with the channel member will be occasionally momentarily gained and then lost. Indeed, where the location of the channel member below the skin is not known by a user of the ultrasonic inspection system 10, the transducers 14 and 16 can be moved about near the skin until the location of the channel member is indicated by the presence of a data pulse in the gate 82. Finding and inspecting the channel member is promoted by maintaining the transducers a distance apart that matches the width of the channel 52, or more particularly, that matches the distance between the first interface portion 48 and second interface portion 50 of the channel member 42.

FIG. 6 represents an inspection scenario in which a two-dimensional mapping referred to herein as a C-scan 104 is partially populated with data related to the condition of a structure under inspection by the ultrasonic inspection system 10. As the transducers are moved about, a C-scan is populated with data related to the amplitudes of signals received by the second transducer 16. In FIG. 6, two pixels of the C-scan 104 are populated with data, whereas in FIG. 7, a C-scan is fully populated. The C-scan of FIG. 7 may be understood by first considering the inspection scenario of FIG. 6 which establishes how particular pixels in a C-scan are correlated with particular positions of the transducers of the inspection system.

In FIG. 6, a mobile inspection device 90 comprises the first transducer 14, the second transducer 16, and a connector 84. The connector 84 maintains the distance between the transducers to match the width of the channel 52 as defined by the distance between the first interface portion 48 and second interface portion 50 of the channel member 42. An axis 86, defined between the transducers, is preferably generally maintained as perpendicular to the axis 88 defined by the elongate channel member 42. The mobile inspection device 90 may be arbitrarily moved along the skin and the transducers 12 and 16 will occasionally oppose respective the interface portions of the channel member as shown in FIGS. 1-4. The mobile inspection device 90 may further comprise a movement encoder such as a track-ball, x-y encoded scan frame, or an optical device so that positions of the mobile inspection device 90 are automatically correlated with pixels of the C-scan 104 by the controller 20.

In FIG. 6, the first transducer 12 is disposed at a location 100 which opposes the first interface portion 48 of the channel member 42, and the second transducer 14 is disposed at a location 102 which opposes the second interface portion 50 of the channel member. A plot 128 (amplitude versus time) having the data pulse 36 confirms the dispositions of the transducers over the channel member similarly as shown for example in FIG. 1. The amplitude of the data pulse 36 in the plot confirms the good condition of the channel member below the transducers. A partially populated C-scan 104 represents the data pulse 36 as a colorized pixel 106. The location of the pixel 106 in the two-dimensional C-scan corresponds to the location of the mobile inspection device 90 along the two-dimensional first surface 44 of the skin 40.

The mobile inspection device 90 may be moved to dispose the first transducer 12 at a location 110 and the second transducer at a location 112. The transducers in such locations do not oppose interface portions of the channel member. A plot 129, like the plot of FIG. 5, shows no appreciable data pulse within the gate 82 because the mobile inspection device 90 was not disposed above the channel member when the plot was produced. The C-scan 104 denotes the empty gate 82 with a blank pixel 108. The mobile inspection device 90 may be moved about along the skin 40 to further populate the C-scan 104 with data. Movements of the device 90, axial movements 114 parallel to the axis 88 of the channel member, and transverse movements 116 perpendicular to the channel member, are correlated with pixel allocations on the C-scan 104. The device 90 may be moved in arbitrary fashion along the skin to populate the C-scan, or may be moved in a raster pattern defined by ordered axial movements 114 and transverse movements 116.

FIG. 7 represents an inspection scenario in which pixels of a C-scan 105 are completely populated with data related to the condition of a structure under inspection by the ultrasonic inspection device 10. The footprints of the first and second interface portions 48 and 50 are shown as respective bands 118 and 119 for illustrative purposes, though it should be understood that real structures under inspection may or may not provide such convenient markings. As in FIG. 6, the colorized pixel 106 represents the findings of the ultrasonic inspection system 10 when the device 10 is disposed above the channel member with the first transducer 12 and second transducer 16 at the respective locations 100 and 102. The blank pixel 108 again represents the findings of the system 10 when the device 90 is disposed away from the channel member with the first and second transducers at the respective locations 110 and 112.

When the mobile inspection device 90 is disposed with the first and second transducers at the respective locations 120 and 122, a reduced data pulse 136 is shown on the plot 130. The mobile device is disposed above the channel member 42, but the channel member may have an irregularity such as flaw 60 shown in FIG. 2, or the channel member may be partially detached from the skin such as shown in FIG. 3. In any event, the reduced data pulse 136 is evidence of a hidden problem in the inspected structure in the vicinity of locations 120 and 122. This evidence is further exhibited in the C-scan 105 in the area 138. In this fully populated C-scan 105, a dark shaded band appears corresponding to positions of the mobile device 90 above undamaged portions of the channel member 42. The band is broken in the area 138 of the C-scan 105 because the area 138 corresponds to the vicinity of the locations 120 and 122 along the skin above a damaged portion of the underlying channel member. The plot 131 exhibits a real-time data pulse 140 received at the current location of the device 90. The darkened pixel 142 demonstrates in the C-scan 105 the good condition of the channel member 42 proximal the device 90.

The pixels of the C-scan 105 may be colored or shaded according to various coloring and shading schemes to denote the amplitudes of data pulses. In FIG. 7, the C-scan 105 entails a scheme that correlates black shading with strong data pulses and correlates blank areas with absent data pulses. That scheme may also correlate increasingly darkened shades of grey with data pulses of increasing amplitudes. Another scheme may map an ordered range of colors to a range of data pulse amplitudes. Preferably, a scheme is chosen that provides a band image along a C-scan in correlation with a channel member hidden opposite a skin from an inspection system. Irregularities in the channel member or its attachment to the skin are then discovered by way of irregularities in the band image along the C-scan.

Thus, as described above with reference to FIGS. 1-7, damage in the channel member 42 or in its attachment to the skin 40 is detected by the ultrasonic inspection system 10. The channel member 42 is inspected using an ultrasonic NDI system disposed on an opposite side of the skin 40 from the channel member. The inspection is accomplished without disposing equipment within the channel 52 which may be inaccessible or may be obstructed with any sort of hardware.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of inspecting a structure, the method comprising:

providing a structure comprising a skin and a channel member, the channel member comprising a first interface portion and a second interface portion each attached to the skin such that a channel surrounded by the skin and channel member is defined;

transmitting an ultrasonic signal into the structure through the skin such that at least a first portion of the signal propagates across the channel member partially about the channel from the first interface portion to the second interface portion;

receiving the first portion of the signal from the structure through the skin; and detecting a defect in the channel member based upon at least the received first portion of the ultrasonic signal wherein the channel member comprises:

a generally planar elongate first web member that comprises the first interface portion;

a generally planar elongate second web member that comprises the second interface portion; and a generally planar elongate cap member attached along opposing interfaces thereof to the first web member and second web member respectively;

wherein transmitting an ultrasonic signal into the structure comprises transmitting an ultrasonic signal into the structure such that at least the first portion of the signal propagates, in sequential order, through the skin, across the first web member, across the cap member, across the second web member, and through the skin.

2. A method according to claim 1, wherein transmitting an ultrasonic signal into the structure through the skin comprises disposing a transmitting transducer to oppose the first interface portion through the skin, and, wherein receiving the first portion of the signal comprises disposing a receiving transducer to oppose the second interface portion through the skin.

3. A method according to claim 2, further comprising moving at least the receiving transducer, wherein detecting a defect in the channel member comprises comparing an output of the receiving transducer at a first position to an output of the receiving transducer at a second position.

4. A method according to claim 2, further comprising moving the transmitting transducer and receiving transducer in concert.

5. A method according to claim 4, wherein moving the transmitting transducer and receiving transducer in concert comprises moving the transmitting transducer and receiving transducer in two dimensions near the skin.

6. A method according to claim 4, wherein detecting a defect in the channel member comprises detecting the defect based upon a C-scan.

7. A method according to claim 4, wherein the first interface portion is attached to the skin such that a first elongate joint is defined, wherein the second interface portion is attached to the skin such that a second elongate joint is defined, wherein the first elongate joint and second elongate joint are essentially parallel, and wherein moving the transmitting transducer and receiving transducer in concert comprises moving the transmitting transducer and receiving transducer at least along an axis parallel to the first elongate joint.

8. A method according to claim 1, wherein transmitting an ultrasonic signal comprises transmitting an ultrasonic signal having a frequency of less than approximately 1.5 million cycles per second.

9. A method according to claim 1, wherein transmitting an ultrasonic signal into the structure comprises directionally transmitting an ultrasonic signal along a propagation axis having at least a component that is essentially perpendicular to the skin.

10. A method according to claim 1, wherein the skin comprises a first surface and a second surface opposite the first surface, wherein the first interface portion and the second interface portion of the channel member are attached to the skin along the second surface such that the channel is defined between the channel member and the second surface, and wherein the method further comprises:

providing a first transducer that transmits the ultrasonic signal into the structure, the first transducer disposed near the first surface of the skin; and providing a second transducer that receives the first portion of the signal from the structure, the second transducer disposed near the first surface of the skin.

11. A method according to claim 10, further comprising measuring the time of flight of the first portion of the signal by measuring the time elapsed between the transmission of the ultrasonic signal by the first transducer and the receipt of the first portion of the signal by the second transducer.

12. The method according to claim 11, wherein the ultrasonic signal is transmitted into the structure by the first transducer such that a second portion of the signal propagates across the skin, wherein the second portion is received by the second transceiver, and wherein the time of flight of the second portion is measured.

13. The method according to claim 12, wherein detecting a defect in the channel member comprises discriminating the second portion from the first portion according to their respective times of flight.

14. The method according to claim 10, wherein detecting a defect in the channel member comprises generating a C-scan image based upon the amplitude of the first portion of the ultrasonic signal.

15. A method of inspecting a stiffener attached to a panel, the method comprising:

providing a panel comprising a first surface and a second surface;

providing an elongate stiffener attached to the second surface of the panel such that an elongate channel surrounded by the panel and the stiffener is defined between the stiffener and the second surface;

disposing an ultrasonic inspection apparatus at a first location near the first surface such that portions of signals transmitted by a first transducer travel partially about the channel by propagating across the stiffener and are received by a second transducer;

measuring the amplitudes of the portions of the signals received by the second transducer at the first location of the ultrasonic inspection apparatus;

disposing the ultrasonic inspection apparatus at a second location near the first surface such that portions of the signals transmitted by the first transducer travel partially about the channel by propagating across the stiffener and are received by the second transducer;

measuring the amplitudes of the portions of the signals received by the second transducer at the second location of the ultrasonic inspection apparatus; and detecting an irregularity in the stiffener by comparing the amplitudes of the signals received at the first location to the amplitudes of the signals received at the second location.

16. A method according to claim 15, wherein the stiffener comprises an elongate first interface and an opposing elongate second interface, wherein the first interface is attached to the second surface of the panel defining a first joint, wherein the second interface is attached to the second surface of the panel defining a second joint that is essentially parallel to the first joint, wherein disposing the ultrasonic inspection apparatus at the first location comprises disposing the first transducer to oppose the first interface through the panel and disposing the second transducer to oppose the second interface through the panel, and wherein disposing the ultrasonic inspection apparatus at the second location comprises disposing the first transducer to oppose the first interface through the panel and disposing the second transducer to oppose the second interface through the panel.

17. A method according to claim 16, further comprising moving the ultrasonic inspection apparatus near the skin such that an axis defined as passing through the first transducer and second transducer is maintained essentially perpendicular to the first joint.

18. A method according to claim 17, wherein moving the ultrasonic inspection apparatus near the skin comprises maintaining a fixed distance between the first transducer and the second transducer, wherein the fixed distance maintained between the first transducer and the second transducer is essentially the same as the distance between the first joint and the second joint.

19. A method according to claim 16, further comprising moving the ultrasonic inspection apparatus such that the first transducer and the second transducer are moved in concert in two dimensions, wherein detecting an irregularity in the stiffener comprises displaying a C-scan.

* * * * *